US010071059B2

(12) United States Patent
van Gessel

(10) Patent No.: US 10,071,059 B2
(45) Date of Patent: Sep. 11, 2018

(54) CO-PROCESSED TABLET EXCIPIENT COMPOSITION ITS PREPARATION AND USE

(75) Inventor: Alexander Wilhelmus van Gessel, Rheinberg (DE)

(73) Assignee: FRIESLANDCAMPINA NEDERLAND HOLDING B.V., Amersfoort (NL)

( * ) Notice: Subject to any disclaimer, the term of this patent is extended or adjusted under 35 U.S.C. 154(b) by 0 days.

(21) Appl. No.: 13/516,706

(22) PCT Filed: Dec. 16, 2010

(86) PCT No.: PCT/NL2010/050855
§ 371 (c)(1),
(2), (4) Date: Aug. 3, 2012

(87) PCT Pub. No.: WO2011/074961
PCT Pub. Date: Jun. 23, 2011

(65) Prior Publication Data
US 2013/0177649 A1    Jul. 11, 2013

(30) Foreign Application Priority Data

Dec. 18, 2009    (EP) .................................... 09179867

(51) Int. Cl.
*A61J 3/00* (2006.01)
*A61K 9/16* (2006.01)
*A61K 9/20* (2006.01)

(52) U.S. Cl.
CPC ............... *A61K 9/2095* (2013.01); *A61J 3/00* (2013.01); *A61K 9/1623* (2013.01); *A61K 9/1635* (2013.01); *A61K 9/1652* (2013.01); *A61K 9/1694* (2013.01); *A61K 9/2018* (2013.01); *A61K 9/2027* (2013.01); *A61K 9/2054* (2013.01); *A61K 9/2059* (2013.01)

(58) Field of Classification Search
None
See application file for complete search history.

(56) References Cited

U.S. PATENT DOCUMENTS

| | | | |
|---|---|---|---|
| 3,079,303 A * | 2/1963 | Raff et al. .................... 424/500 |
| 3,344,030 A | 9/1967 | Stevens et al. | |
| 5,006,345 A | 4/1991 | Lang | |
| 5,630,871 A * | 5/1997 | Jordan ..................... A01C 1/06 106/162.7 |
| 6,514,524 B1 | 2/2003 | Saslawski et al. | |
| 2001/0024641 A1* | 9/2001 | Yang .............................. 424/46 |
| 2006/0165793 A1* | 7/2006 | Ukai ............................ 424/470 |
| 2006/0246135 A1 | 11/2006 | Nagi et al. | |
| 2006/0247234 A1 | 11/2006 | Nagi et al. | |
| 2007/0086689 A1 | 4/2007 | Qiu et al. | |
| 2008/0311205 A1* | 12/2008 | Habib et al. .................. 424/488 |
| 2009/0081308 A1* | 3/2009 | Kussendrager .......... C13K 5/00 424/499 |
| 2010/0178340 A1* | 7/2010 | Koo et al. ..................... 424/465 |

FOREIGN PATENT DOCUMENTS

| | | |
|---|---|---|
| WO | WO-97/44014 A1 | 11/1997 |
| WO | WO-01/41744 | 6/2001 |
| WO | WO-02/03963 | 1/2002 |
| WO | WO-2004/110406 A1 | 12/2004 |
| WO | WO-2007/031933 A2 | 3/2007 |
| WO | WO-2008/020990 | 2/2008 |
| WO | WO 2009022821 A2 * | 2/2009 ............. A61K 31/35 |
| WO | WO-2009/112287 | 9/2009 |

OTHER PUBLICATIONS

Vromans, H., et al. "Studies on tableting properties of lactose. VII. The effect of variations in primary particle size and percentage of amorphous lactose in spray dried lactose products." International journal of pharmaceutics 35.1 (1987): 29-37.*
International Search Report for PCT/NL2010/050855—dated Mar. 22, 2011.

* cited by examiner

*Primary Examiner* — John Pak
*Assistant Examiner* — Daniel L Branson
(74) *Attorney, Agent, or Firm* — Gilberto M. Villacorta; Sunit Talapatra; Foley & Lardner LLP

(57) ABSTRACT

The invention pertains to a co-processed excipient composition suitable for tableting, said composition comprising at least one filler-binder, at least one disintegrant, and at least one lubricant which have been subjected to granulation together, and said composition partially or completely coated with lactose, preferably in crystalline form. The inventors have overcome the prejudice against the use of lubricants in tableting excipient compositions early in the tableting process. It was found that the alleged detrimental affects of the lubricant in terms of binding and disintegration could readily be controlled in a excipient composition wherein the lubricant is co-processed in the matrix, and the composition is provided with a lactose coat.

10 Claims, 4 Drawing Sheets

CO-PROCESSED TABLET EXCIPIENT COMPOSITION ITS PREPARATION AND USE

CROSS-REFERENCE TO RELATED APPLICATION(S)

This application is the National Phase of International Patent Application No. PCT/NL2010/050855, filed Dec. 16, 2010, published as WO 2011/074961, which claims priority to European Application No. 09179867.8, filed Dec. 18, 2009. The contents of these applications are herein incorporated by reference in their entirety.

FIELD OF THE INVENTION

The present invention pertains to a co-processed tablet excipient composition, its preparation and its use in tableting.

BACKGROUND OF THE INVENTION

In the pharmaceutical industry the most commonly employed means to deliver active pharmaceutical ingredients (hereinafter "API" or "APIs") is the tablet, which may be obtained through the compression of appropriately formulated powders. Conventional, compressible mixtures are typically obtained by the blending of an API and suitable excipient materials. These excipients may include diluents or fillers/carriers, binders or adhesives, disintegrants, glidants or flow promoters, colours, flavours and mixtures thereof. A glidant is a substance that is added to a powder to improve its flowability into the tableting device.

As mentioned in WO2008/020990 these materials may simply be blended, or may be granulated in either the dry or wet state. Once mixing is complete, a lubricating excipient is added and the material compressed into tablets. WO2008/020990 itself is striving for a universal excipient blend that maximizes the ability of APIs to be formulated without adversely affecting its safety and efficacy profiles. The blend would be mixed with an API and optionally a lubricant, then compressed into tablets. This is also confirmed in U.S. Pat. No. 3,344,030. The flow charts at page 14, 15 and 17-19 of WO 2007/031933 perfectly demonstrate that a lubricant should be added after granulation and milling of the granule, only to be followed by compaction. WO01/41744, at page 31 in particular, teaches to prepare pellets by coating spheroids containing an API and pre-mixed excipient components with a suspension containing magnesium stearate. Independent on the way of tableting, a lubricant is blended with carrier and active compound only just prior to compression. Likewise, U.S. Pat. No. 5,006,345 provides a direct tableting auxiliary based on lactose powder mixed intimately with a binder, and a tablet disintegrant agent. After mixing these with the API, a lubricant is only then added and the mixture is pressed to produce tablets. WO 97/44014, US 2006/0246135, WO 2007/086689, U.S. Pat. No. 6,514,524 and WO 02/03963 teach similarly. In all events, a lubricant is again added immediately preceding compaction, after pre-mixing of the other excipient components.

Outside the field of providing ready-to-use co-processed tablet excipient components, WO 2004/110406 and US 2006/0247234 both disclose processes in which the API, excipients and lubricant are mixed altogether.

In the field, however, a lubricant is deemed necessary to realise release of the compressed form or tablet from the device. However, at the same time it is believed that the lubricant could affect the necessary binding between the various carrier components and, in the case of hydrophobic lubricants such as magnesium stearate, tablet disintegration properties negatively. Regarding the binding properties, the reasons would rest in the tendency of lubricants to coat the excipient components, thus preventing these from adhering to one another. Also, a hydrophobic lubricant coat repels water which plays an important role in disintegration. Therefore, the use of lubricant is postponed until mixing of all components has been achieved, so as to minimize contact time between lubricant and other tablet components prior to the actual compression step.

In the art, WO 2009/112287 recently disclosed that the lubricant can already be added to the co-processing step, thus providing a ready-to-use excipient composition which would conveniently require only the steps of adding the API(s) and compression, and still expedite ejection from the tableting die. Despite the use of lubricant at an earlier processing stage, the die ejection force and tablet force are excellent. However, to yield these properties, the process of WO 2009/112287 involves spraying of the lubricant onto the cogranulated components, thus creating a lubricant coat covering the granules. It thus continues to feed the skilled person's belief that the lubricant should make direct contact with the die, which can only be achieved when spraying it as an outside layer to the excipient composition.

In the art, there is however the continuous need for further optimizing the process for producing ready-to-use co-processed excipient compositions.

BRIEF DESCRIPTION OF THE DRAWINGS

FIG. 4C is a magnified version of the co-processed excipient in FIG. 4B.

FIG. 4A shows the individual particles each having their own characteristics.

SUMMARY OF THE INVENTION

Figure 1:
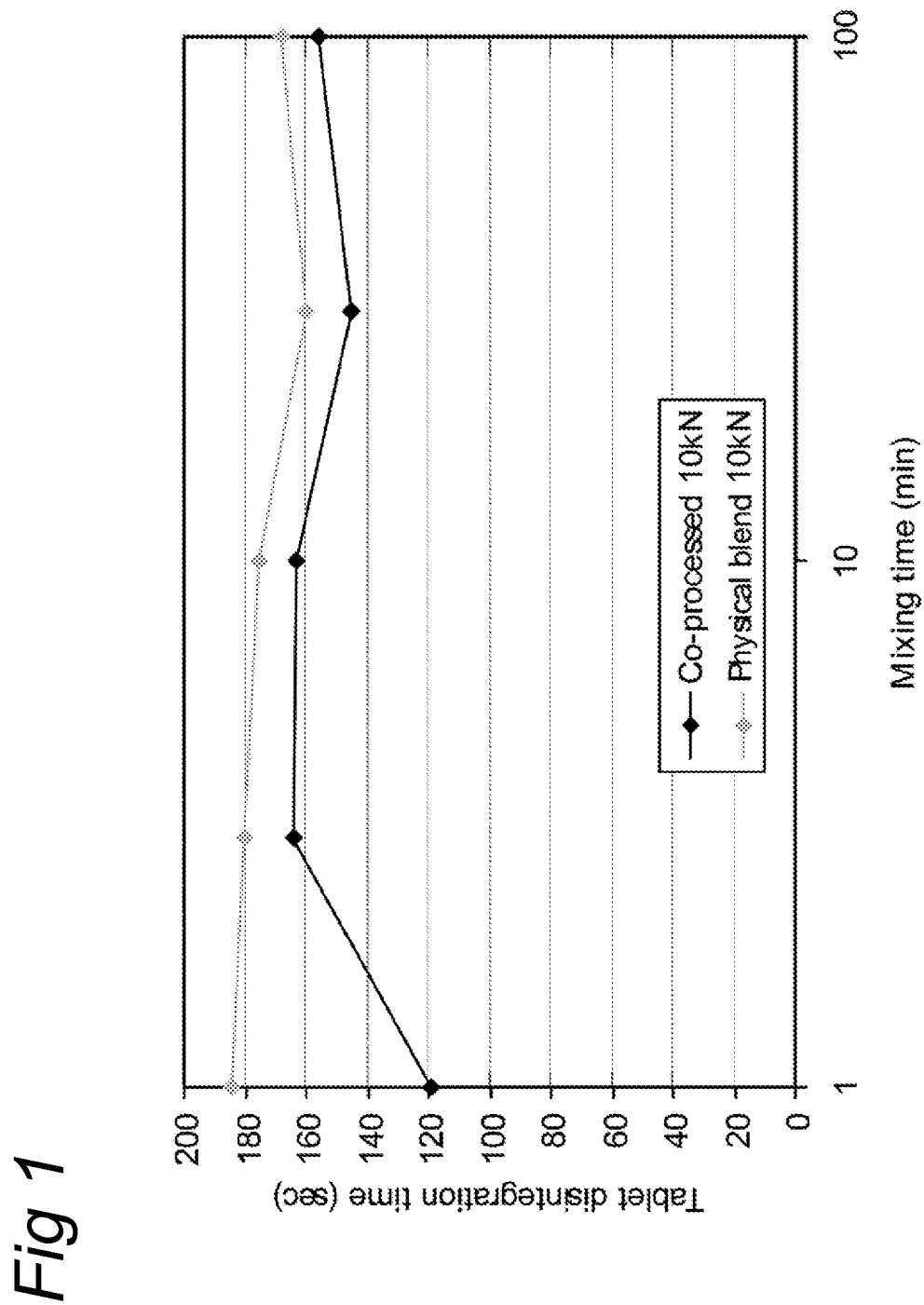
FIG. 1 shows the disintegration time of the tablets of the co-processes excipient and the physical blend for the different mixing times on a logarithmic scale.

The inventors have overcome the prejudice against the use of lubricants as a homogeneous mixture with at least filler-binder and disintegrant in tableting co-processed excipient compositions, and found there is no need for the lubricant to make immediate contact with the die. It was found that the alleged detrimental affects of the lubricant in terms of binding and disintegration could readily be controlled in a excipient composition wherein the lubricant is co-processed in the actual granulation. This finding renders spraying of the lubricant onto the excipient components during granulation unnecessary. Advantageously, instead of lubricant, the skilled person may choose to spraying a lactose solution onto the other components in fluid bed technology, thus yielding the granules with lactose on the outside. Due to the excellent water solubility characteristics and density of lactose, its presence on the outside favourably contributes to the binding and flowability, further enhancing disintegration and thus eliminating the need for glidants at least to a large extent, to levels of lower than 0.25% of the excipient composition.

Contrary to the art's belief, the fact that the lubricant is thus not directly on the outside does not adversely affect the tablet and ejection forces, and thus renders it possible to make use of the benefits of lactose Although the inventors do not wish to be tied down to any theory, the incorporation of the lubricant into the matrix rather than on the outside is believed to ease production of tablets and still avoid loss of compactability due to non-adhering lubricant film.

Disintegration was thus found not to be affected and compactability to a lesser extent than in a non-incorporated version, i.e. a physical mix of unaggregated components. The compactability and disintegration results are shown in the accompanying examples and FIGS. 1 and 2. The co-processed excipient with a lactose coating according to the present invention already incorporating the lubricant inside the ready-to-use co-processed excipient composition in a homogeneous mixture with at least disintegrant(s) and filler-binder(s) provides a simplified method of formulation as compared to the traditional methods of tablet formulation. All but the API(s) are co-processed into a tableting excipient formulation, which is ready-to-use and marketed for tableting together with the API(s).

DETAILED DESCRIPTION OF THE INVENTION

The invention thus pertains to a co-processed excipient composition comprising granules including at least one lubricant, one or more filler-binder(s) and one or more disintegrant(s), said granules (preferably at least partially) coated with a lactose, said lactose preferably in crystalline form, preferably in the monohydrate and/or anhydrous form.

Worded differently, the invention pertains to an excipient composition wherein at least one lubricant is co-processed with conventional excipient components into granules, typically at least one or more filler-binder(s) and one or more disintegrant(s), and wherein lactose is on the outside of the granules comprising at least one lubricant, disintegrant and filler-binder. The components have been granulated together, simultaneously.

Coat

The surface of the granules coated with lactose may be described as "coarse", providing more surface are for compaction, caused by the crystalline nature of the coating material. It is preferred that the granules are at least partially coated, for instance as distinct islands. In other words, the coating or coating layer may have an open (porous) or closed appearance or structure, as demonstrated by the accompanying SEM pictures. In one embodiment, the lactose forms a continuous coating layer.

In the prior art case of coating with a lubricant a much smoother surface is found. Within the context of the invention, the terminology "coat" merely describes that the lactose adheres to the outer or top surface of the granules.

The excipient composition according to the invention is agglomerated, and is suited for tableting (i.e. "untableted", to still produce tablets). The excipient composition may be characterized by being uncompressed or compressed to a lesser extent than considered sufficient for producing tablets.

The terminology "co-processed excipient (composition)" is construed to mean a homogeneous, non-segregating, free-flowing blend or mixture of components suitable for subsequent tableting with one or more active pharmaceutical ingredients. In the field, 'co-processing' is a well-recognized term, meaning that one or more excipient components are incorporated into the particle structure of another excipient component using processes such as co-drying, agglomerating or granulating. The excipient composition is physically modified but the chemical structure of the components remains unaltered. It is preferred that at least the filler-binder(s), lubricant(s) and disintegrant(s) are subjected to granulation or agglomeration together, preferably wet granulation. The "co-processed excipient" may also be characterized as an agglomerate, or a granulate, as opposed to a mere physical blend of the individual excipient components that is established by the mere mixing of the individual excipient components. The agglomerate or granulate is preferably further characterised in that the granule is of irregular shape with a particle size of typically <0.500 mm (based on the largest cross-section). Co-processing is sometimes referred to as combining known excipient components at sub-particle level. In the present case, it includes the lubricant(s).

Self-explanatory, inherent to the terminology "excipient composition", the co-processed excipient composition itself is free from any API(s). It is in powdered form, preferably formed from particles with irregular shape and having a size typically less than 0.500 mm, preferably having a water content of less than 8%, more preferably less than 7% based on the total weight of the co-processed excipient composition (crystal water included). In terms of flowability, the co-processed excipient composition preferably exhibits a poured bulk density of about 400-600 g/l, and/or a tapped bulk density of about 400-700 g/l.

Compared to the prior art, the choice and amount of lubricant are conventional. The amount of lubricant(s)—based on the total dry weight of the co-processed excipient—typically ranges between 0.2 and 2.2 wt %, preferably up to 1.0 wt. Common minerals like talc or silica, and fats, e.g. vegetable stearin, magnesium stearate, calcium stearate, stearic acid, sodium lauryl sulphate, or sodium stearyl fumarate are the most frequently used lubricants in tablets. Pharmaceutically acceptable stearate salts (and their conjugated acids) and stearyl fumarate (sodium or potassium salt), are particularly preferred.

Filler-binders hold the ingredients in a tablet together. Filler-binders ensure that tablets and granules can be formed with required mechanical strength, and give volume to low active dose tablets. The amount of filler-binder(s)—based on the total dry weight of the co-processed excipient—typically ranges between 78-98.8 wt %, preferably between 90-97.0 wt %. Filler-binders are usually starches, sugars, cellulose or modified cellulose such as microcrystalline cellulose (MCC), hydroxypropyl cellulose, lactose, or sugar alcohols like xylitol, lactitol, mannitol, sorbitol or maltitol.

For reasons outlined above, it is particularly preferred that the co-processed excipient comprises lactose, preferably both inside the granules and on their surface. In either case, the lactose is preferably in the monohydrate and/or anhydrous form. The lactose is preferably the predominant filler-binder in the composition. Lactose also fulfils the role of a diluent present in tablets. The lactose is preferably in agglomerated form. Good results are obtained with a milled lactose type, such as Pharmatose 200M, commercially available with DMV-Fonterra Excipients (Germany).

Disintegrants ensure that when the tablet is in contact with water, it rapidly breaks down into smaller fragments, thereby facilitating dissolution. The amount of disintegrant(s)—based on the total dry weight of the co-processed excipient—typically ranges between 1.0-10.0 wt %, preferably between 2.0-6.0 wt %. Examples of disintegrants include crosslinked polyvinyl pyrrolidone, sodium starch glycolate, crosslinked sodium carboxymethyl cellulose (crosscarmellose). Potato-derived sodium starch glycolate is the most preferred. Good results are obtained with Primojel®, commercially available from DFE (DMV-Fonterra Excipients Germany). Another suitable disintegrant is croscarmellose sodium sold under the name Primellose® (DMV-Fonterra Excipients (Germany)).

In a preferred embodiment the co-processed excipient comprises lactose (preferably in an amount of 40-70%), sodium starch glycolate, microcrystalline cellulose and a lubricant. Even more preferred, the co-processed excipient comprises 40-70% lactose, 20-50% MCC, 1-10% crosslinked sodium starch glycolate, 0.2-2% lubricant.

The co-processed excipient suitable for tableting is supplied in packaged form, preferably provided comprised in (conventional) paper bags or drums (typically with PE inner liners). In one aspect, the invention thus pertains to bags or drums comprising the co-processed excipient according to the present invention.

In accordance with the present invention, the co-processed excipient according to the present invention will allow for the formulation of a wide range of APIs for tableting, thereby facilitating development of a solid dosage delivery device. The co-processed excipient of the present invention may further include optional components, for example glidants (e.g. colloidal silicon dioxide), colors, flavoring agents and mixtures thereof, as are well known in the art. These other components in the co-processed excipient may be included at conventional levels as is well known in the art.

The invention furthermore relates to a method or process of preparing a co-processed excipient as described above, comprising i) providing a mixture containing at least one disintegrant, one filler-binder and at least one lubricant; and ii) agglomerating or granulating said mixture (i.e. co-processing) by means of fluid bed agglomeration, wherein a lactose solution is sprayed onto the fluid bed. This creates the final homogeneously mixed, non-segregating, free-flowing final co-processed agglomerated excipient wherein the disintegrant and lubricant is (partially or completely) covered by lactose.

Fluid bed granulation is a special type of wet granulation, wherein granulation and drying are carried out in the same chamber, and wherein drying starts while agglomerates are being formed. A lactose solution is sprayed from a nozzle, while simultaneously fluidising the powder particles in a stream of air. Sufficient liquid is sprayed to produce granules of the required size, at which point the spray is turned off, but the fluidizing air flow continues in an after-drying step. The combination of granulation and drying in one vessel enables better control of temperature and drying rate.

By bringing the lubricant, disintegrant, filler-binder and other excipient ingredients into contact with a lactose solution during wet granulation, the binding between the excipient components and therewith the strength of the agglomerates is enhanced. It is preferred to add the lactose-containing 'binder' solution stepwise or continuously, most preferably continuously, wherein the moisture supply rate is chosen such that it roughly equals the rate at which free moisture disappears again from the granulator due to drying. Overall, the free moisture content stays within the above-mentioned limits, more preferably it remains about constant during supply of the binder solution.

The lactose or binder solution contains a non-toxic solvent which must be volatile so that it can be removed by drying. Typical solvents include water, ethanol and isopropanol, and combinations thereof. The lactose solution preferably comprises between 5 and 60 wt % of lactose, based on the total weight of the binder solution, and more preferably between 10 and 40 wt %. If the lactose concentration in the binder solution is above 60 wt %, the solution becomes very viscous and spraying becomes difficult.

The invention also pertains to mixing the co-processed excipient with an active pharmaceutical ingredient to form an active pharmaceutical ingredient blend, and tableting the active pharmaceutical ingredient blend to form a pharmaceutically acceptable tablet.

Regardless of the method of production, the co-processed excipient may be mixed at levels ranging from about 10 to 99.9 percent by weight with at least one API.

In an illustrative, non-limiting embodiment, the co-processed excipient is produced by mixing the components and then processing using wet granulation that is well known to those skilled in the art. In a wet granulation process, the component powders are blended, and then wetted to the appropriate consistency with a granulating lactose-containing fluid. The wetted mass is then extruded through a screen, dried to the appropriate water content, milled to the desired particle size and optionally sieved into the desired mean particle size.

Throughout the specification, all percentages are weight/weight based on the dry weight of the excipient blend, unless stated otherwise.

EXAMPLES

Example 1. Manufacture of a Co-Processed Excipient Composition

A co-processed excipient composition was produced by addition of: 261 g Pharmatose® 200M (lactose, a filler/binder, from DFE), 180 g Pharmacel 101® (MCC type, a filler/binder, from DFE), 30 g Primojel® (disintegant, DFE) and 3 g magnesium stearate (lubricant, from Fagron) to a fluid bed agglomerator (Agglomaster AGM-2-PJSD, Hosokawa, Japan) and agglomerating the mixture with 126 g lactose dissolved in 140 ml water. The liquid filler-binder is added to the powder bed over a period of 10 minutes before drying for another 10 minutes. The resulting co-processed excipient is then pre-compressed at a pressure of 10 bar in order to increase the density of the material. It is noted that pre-compressed is not to be confused for the actual tablet compression step at far higher pressures and known to the person skilled in the art.

Example 2. Tableting

To test the influence of the mixing time on the tablet functionality of the co-processed excipient composition, five separate batches of 500 g co-processed excipient according to example 1 were blended in a Turbula T2C (WAB, Switzerland) for 1, 3, 10, 30 and 100 minutes. In each case, the mixed excipient composition was then compressed with 10 kN force on a Rotab-T (Luxner, Berlin, Germany) rotary press with rotary feed frame into 9 mm, 250 mg tablets. These tablets were left to relaxate before testing the disintegration time and tablet crushing strength the following day.

As reference, five blends of SuperTab 14SD® (lactose, filler/binder from DFE) with Pharmacel 102® (a MCC type, filler/binder, from DFE) and Primojel® (DFE) were prepared by blending the ingredients in a Turbula T2C (WAB, Switzerland) rotating at 90 RPM for 8 minutes before adding the magnesium Stearate (Fagron, Germany) and mixing for another 1, 3, 10, 30 or 100 minutes. These are referred to as the 'physical blend' (not subjected to co-processing). Tablets were made from these blends likewise.

Figure 2:
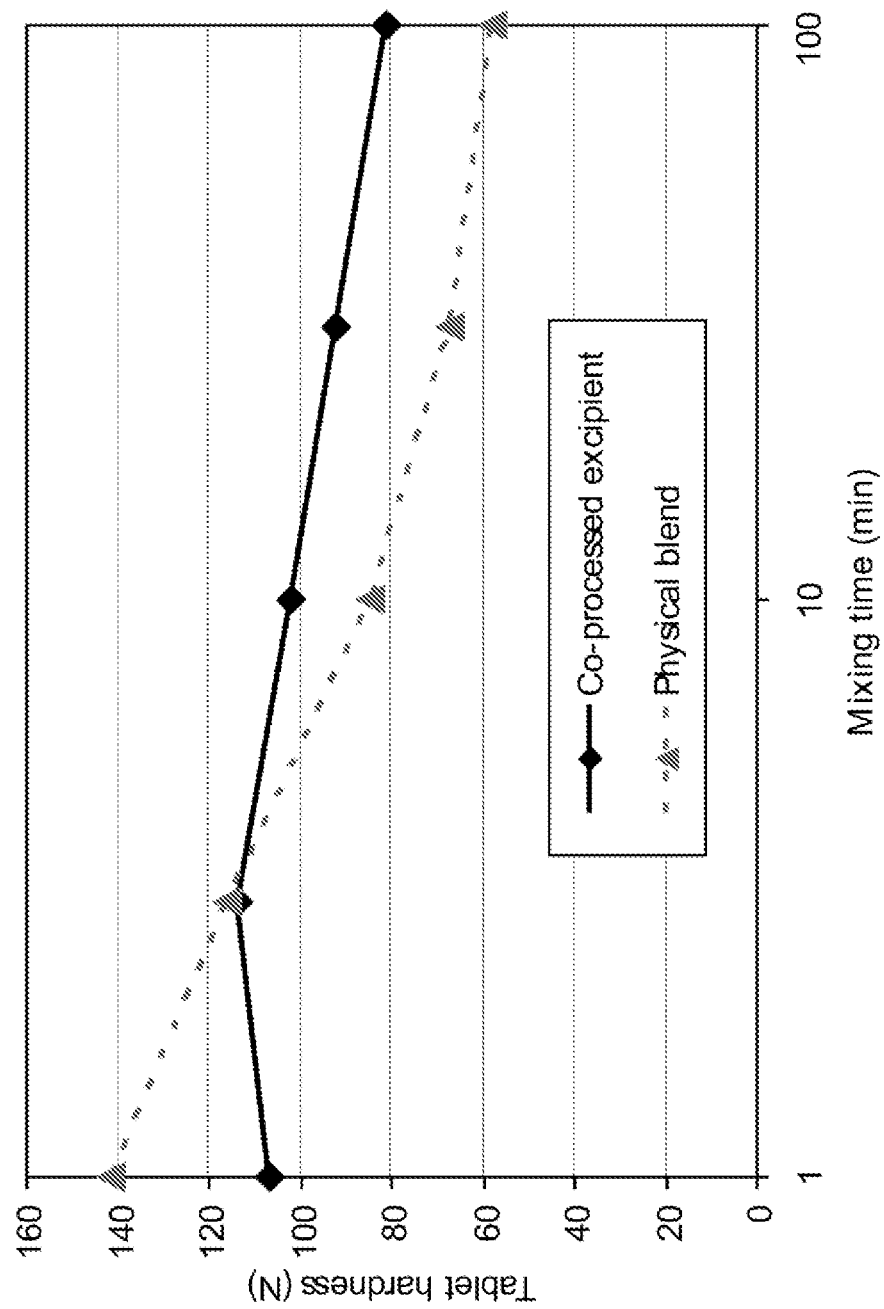
FIG. 2 shows the tablet crushing strength of the tablets of the co-processes excipient and the physical blend for the different mixing times on a logarithmic scale.

FIG. 1 shows the disintegration time of the tablets of the co-processed excipient and the physical blend for the different mixing times on a logarithmic scale. FIG. 2 shows the tablet crushing strength of the tablets of the co-processed excipient and the physical blend for the different mixing times on a logarithmic scale. FIGS. 1 and 2 show that, upon inclusion of the lubricant into the co-processed matrix of other excipients, no significant influence of mixing time is observed in terms of disintegration time. Surprisingly, the tablet hardness of the tablets made with the co-processed excipient is significantly less sensitive to prolonged mixing than observed for those made using the physical blend of the individual components.

Figure 3:
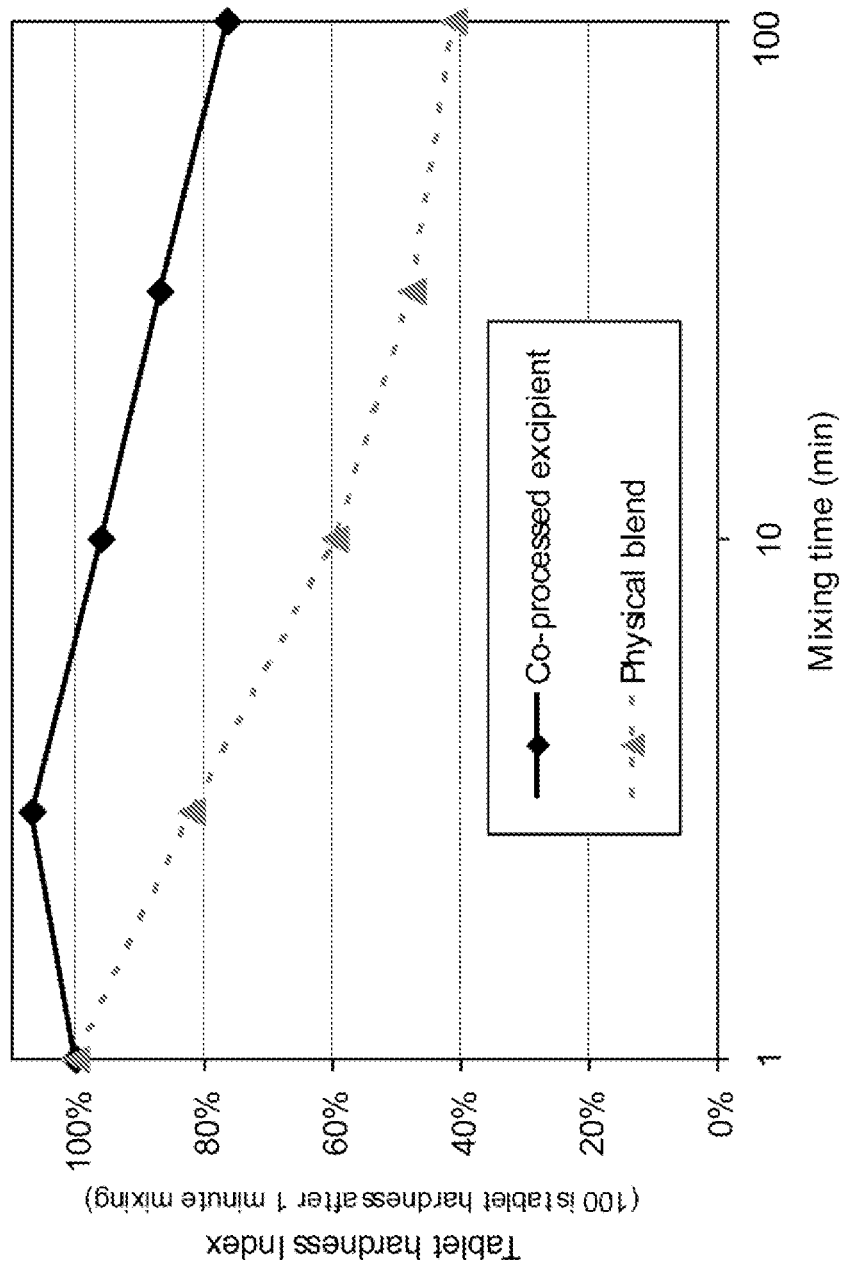
FIG. 3 shows the pronounced effect whereby the tablet hardness of the tablets made with the co-processed excipient is significantly less sensitive to prolonged mixing than observed for those made using the physical blend of the individual components.

This surprising effect is even more pronounced in FIG. 3, where the hardness as a function of the mixing time is indexed to 100 at the hardness after only 1 minute of mixing. It shows a drastic reduction of the tablet hardness over the following 99 minutes of nearly 60% for the physical mix, whereas the co-processed excipient only loses slightly more than 20% of its compactability. Although the inventors do not wish to be bound by any theory, it is believed that the difference in lubricant sensitivity between the co-processed excipient and the physical blend may be caused by the fact that the lubricant is incorporated within the non-segregating matrix of the co-processed excipient and therefore does not form the non-adhering lubricant film as quickly.

This is also an advantage over the process according to WO 2009/112287, where a ready-to-use excipient composition is disclosed having a lubricant coat.

Example 3. SEM

Figure 4A:
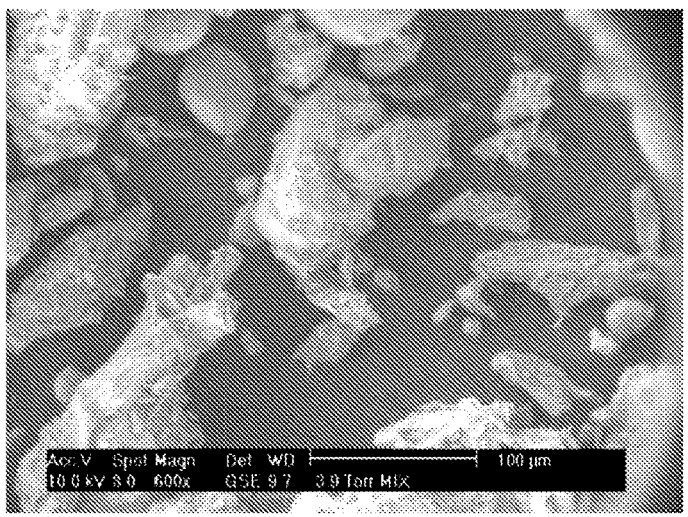
FIGS. 4A-4C compare the physically mixed sample (A) with the co-processed excipient (B).
Figure 4B:
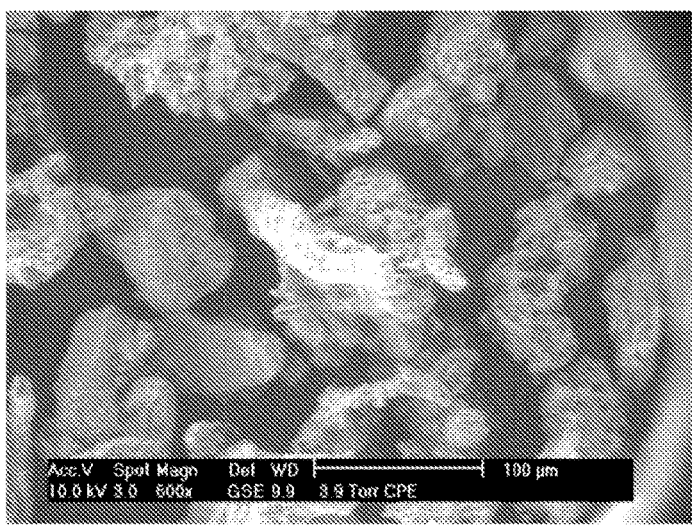
Figure 4C:
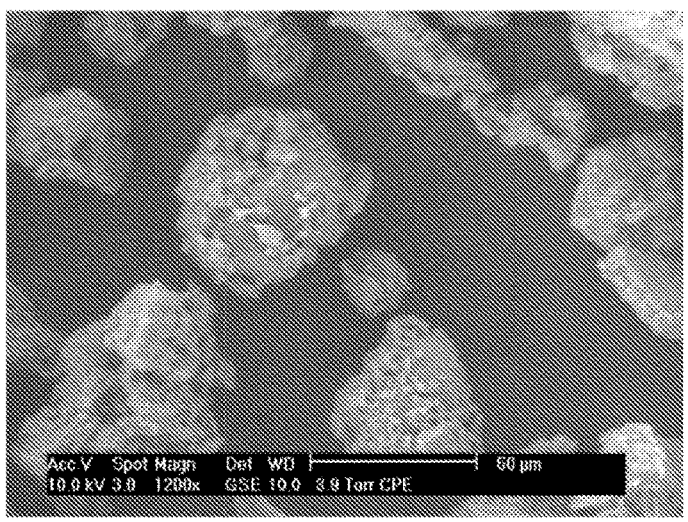

To show the influence of the process of the invention, scanning electron microscope (SEM) was used to take pictures. FIGS. 4A-C compare the physically mixed sample (A) with the co-processed excipient (B). FIG. 4C is a magnified version of the co-processed excipient in FIG. 4B.

FIG. 4A shows the individual particles each having their own characteristics. All are uncoated. The SEM of the co-processed excipient first of all clearly shows the creation of the coarse coat of lactose crystallites and secondly the size enlargement of individual particles resulting from the agglomeration of multiple particles.

The invention claimed is:

1. A pharmaceutical tablet excipient composition, comprising granules comprising, based on total dry weight of the composition, a homogeneous mixture of:
    (a) 78-98.8% of at least one filler-binder;
    (b) 1-10% of at least one disintegrant selected from the group consisting of crosslinked polyvinyl pyrrolidone, crosslinked sodium starch glycolate (SGG), and crosslinked sodium carboxymethyl cellulose, and
    (c) 0.2-2% of at least one lubricant,
    wherein the granules comprise 40-70% of lactose monohydrate, are free of any active pharmaceutical ingredient and are at least partially spray-coated with crystalline lactose.

2. The pharmaceutical tablet excipient composition according to claim 1, wherein the disintegrant is crosslinked sodium starch glycolate (SSG).

3. The pharmaceutical tablet excipient composition according to claim 1, comprising 20-50% of MCC and 1-10% cross-linked sodium starch glycolate, based on total dry weight of the composition.

4. The pharmaceutical tablet excipient composition according to claim 1, wherein the granules are coarse or irregularly shaped with an average particle size of lower than 0.500 mm.

5. A pharmaceutical composition comprising the pharmaceutical tablet excipient composition according to claim 1 and an active pharmaceutical ingredient.

6. The pharmaceutical tablet excipient according to claim 1, wherein the crystalline lactose is in monohydrate and/or anhydrous form.

7. The pharmaceutical tablet excipient according to claim 3, wherein the filler comprises microcrystalline cellulose (MCC).

8. A process of preparing a pharmaceutical tablet excipient composition free of any active pharmaceutical ingredient according to claim 1, the method comprising:
    (a) granulating together in a fluid bed granulator the at least one filler-binder, the at least one disintegrant, and the at least one lubricant, to form granules; and
    (b) spraying a lactose solution onto the granules in the fluid bed granulator to aid in granulation and coat the granules, at least partially, with crystalline lactose; thereby providing said pharmaceutical tablet excipient composition.

9. The process according to claim 8, wherein the solution contains a solvent selected from water, ethanol, isopropanol and combinations thereof.

10. A tableting process comprising:
    (a) mixing the pharmaceutical tablet excipient composition according to claim 1 with an active pharmaceutical ingredient and without additional lubricant to form an active pharmaceutical ingredient blend, and
    (b) tableting said active pharmaceutical ingredient blend.

* * * * *